United States Patent
Kownacki et al.

[11] Patent Number: 5,816,812
[45] Date of Patent: Oct. 6, 1998

[54] DENTAL IMPLANT FIXTURE

[75] Inventors: Charles D. Kownacki, Erie, Pa.; Wade W. Prescott, Vista, Calif.; Rick A. Buss, Dallas, Tex.

[73] Assignee: Osteomed Corporation, Glendale, Calif.

[21] Appl. No.: 279,486

[22] Filed: Jul. 22, 1994

[51] Int. Cl.$^6$ .................................................. A61C 8/00
[52] U.S. Cl. .......................................... 433/174; 433/173
[58] Field of Search .................................. 433/172, 173, 433/174, 175, 176

[56] References Cited

U.S. PATENT DOCUMENTS

| | | | |
|---|---|---|---|
| 4,324,550 | 4/1982 | Reuther et al. | 433/174 |
| 5,061,181 | 10/1991 | Niznick | 433/174 |
| 5,078,607 | 1/1992 | Niznick | 433/174 |
| 5,199,873 | 4/1993 | Schulte et al. | 433/174 |
| 5,269,685 | 12/1993 | Jörnéus et al. | 433/174 |
| 5,427,527 | 6/1995 | Niznick et al. | 433/174 |
| 5,435,723 | 7/1995 | O'Brien | 433/174 |
| 5,527,183 | 6/1996 | O'Brien | 433/174 |

*Primary Examiner*—Nicholas D. Lucchesi

[57] ABSTRACT

A self-tapping dental prosthetic implant has a blunt leading end, a tapered first section which has a uniform minor diameter and a uniformly increasing major diameter, a second section having uniform minor and major thread diameters, a third section with a uniform major thread diameter and a outwardly tapering minor diameter and a fourth section which has a diameter larger than any other segment and a relatively low profile (i.e., short axial length). A thread-cutting groove extends over a substantial portion of the threaded length of the implant. A stepped drill with a tip having a large included angle is used to drill a pilot hole permitting anchoring in the proximate and distal portions of cortical bone by the threaded implant.

8 Claims, 4 Drawing Sheets

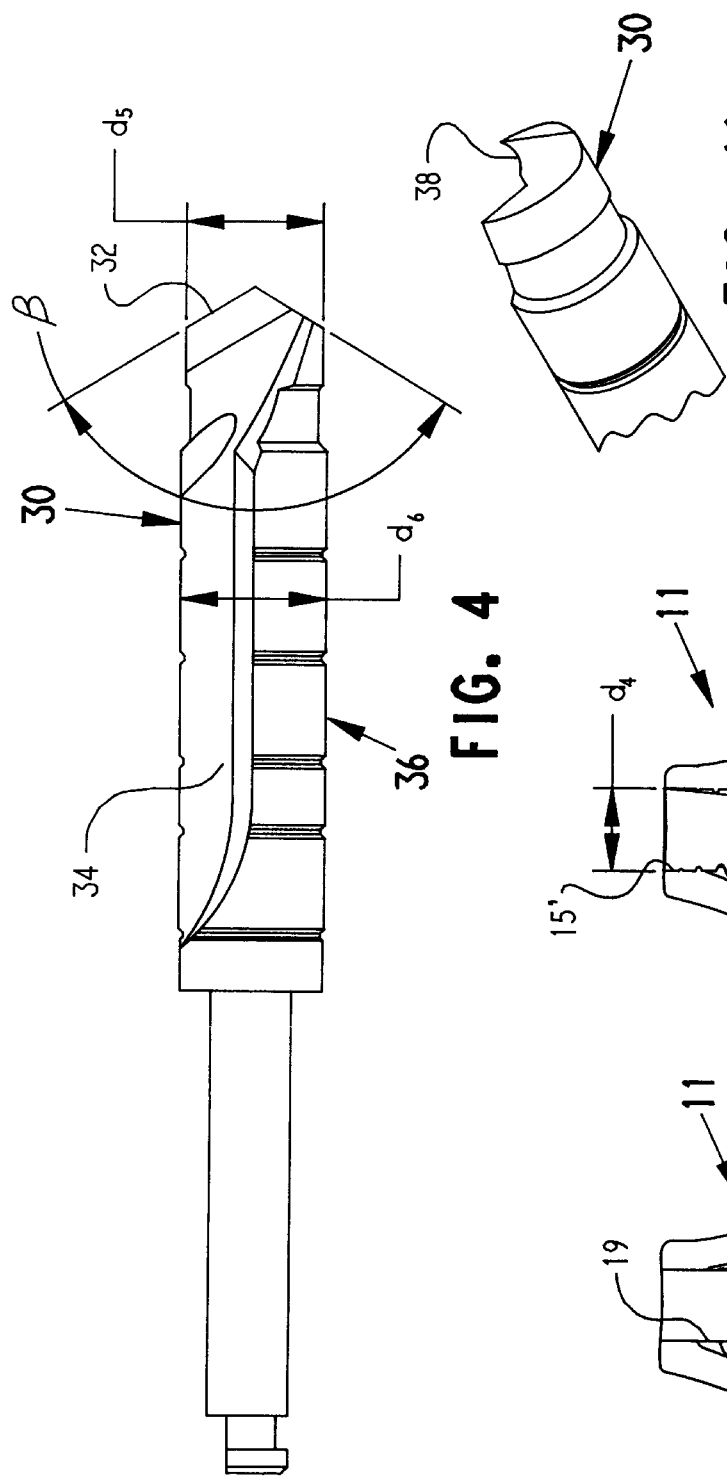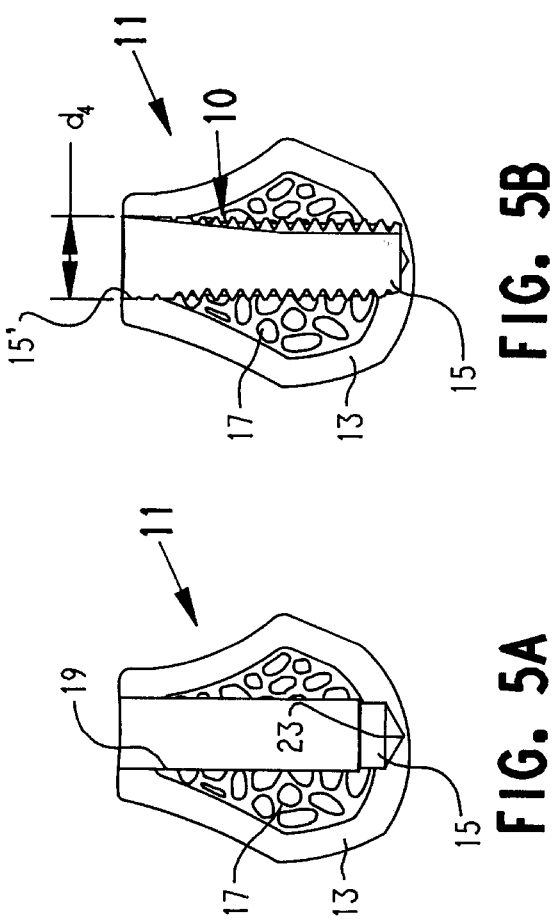

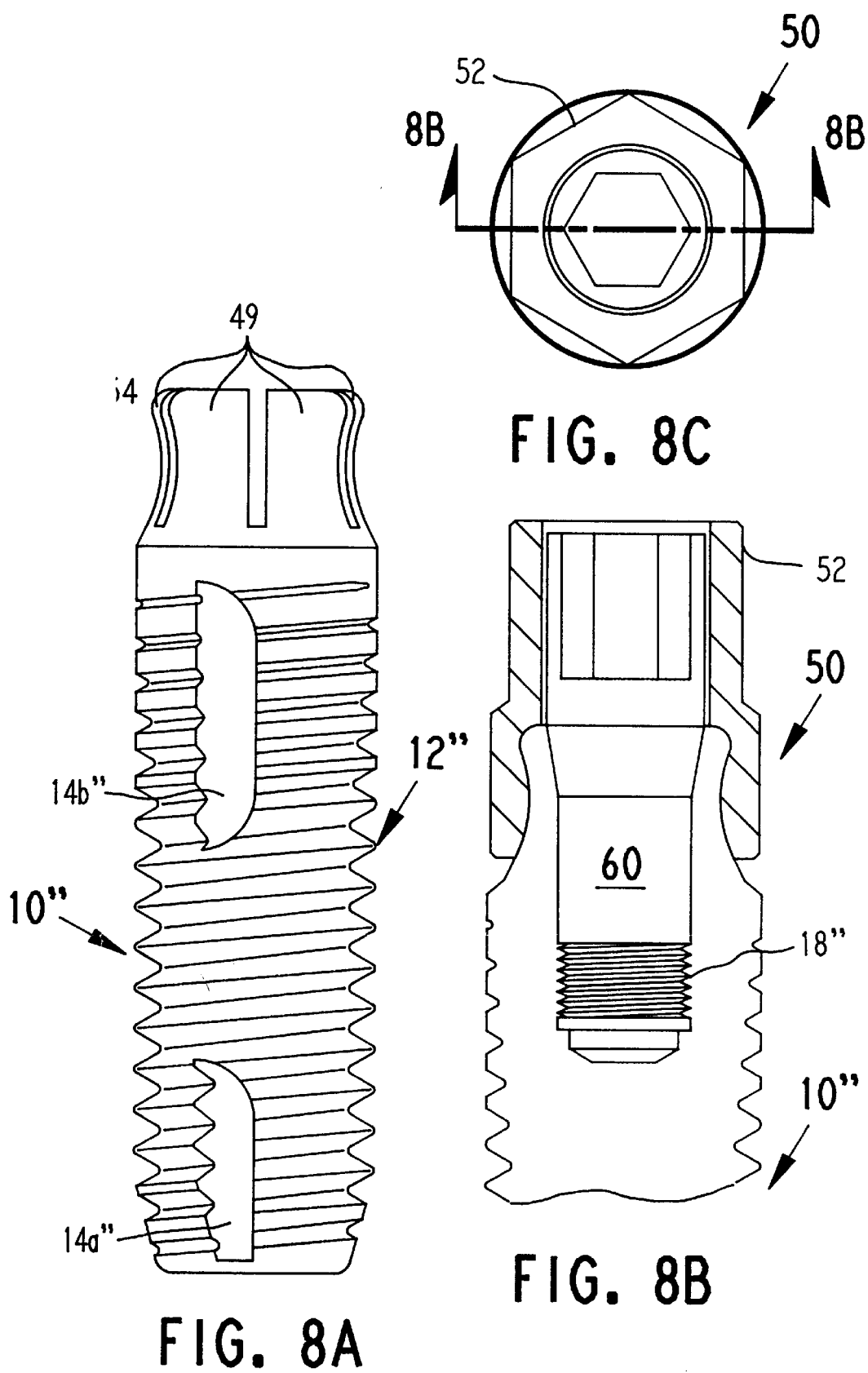

DENTAL IMPLANT FIXTURE

BACKGROUND AND SUMMARY OF THE INVENTION

The present invention is directed to an implantable dental fixture. The fixture is preferably made of a biomechanical material such as titanium or a titanium alloy. This fixture is designed to be implanted in the maxilla or mandible of a patient and becomes the base, or root, for an artificial tooth or denture to be mounted thereon. This invention relates to the implant fixture itself and the drill tool geometry that is used to remove bone to form a pilot hole for the fixture. Commonly assigned U.S. patent application Ser. No. 07/964,747 filed Oct. 22, 1992, now U.S. Pat. No. 5,302,125, which is directed to attachment and adjustability features between the fixture and the abutment, is hereby incorporated by reference.

In some other implant fixture designs, specifically other self-tapping versions, a hole is bored into the bone at a diameter approximating the minor or base diameter of the thread. The top portion of the hole is counterbored or otherwise pre-enlarged to the major diameter of the implant fixture so that a relatively wide unthreaded portion of the implant can be placed into the enlarged hole with a precise fit in order to prevent any bacterial leakage (known as micro-leakage) into the surgical site. The fit between the implant fixture and hole is very important to the healing of and integration of the implant fixture into the bone tissue. This procedure, although somewhat effective, does not take advantage of the hard cortical bone layer that surrounds the perimeter of the mandible and maxilla as a medium in which to anchor.

The present invention uses the very dense cortical bone layer to support the implant fixture with integral self-tapping screw threads. The hole diameter for the self-tapping implant fixture is approximately the pitch diameter of the thread. Pre-enlarging of the top portion of the hole is not necessary with the system of the present invention. The surgical drill has a smaller diameter tip to penetrate the inferior border of cortical bone for support. This design does not simply rely just upon the use of cancellous (soft spongy) bone for mechanical stability. Rather, the present implant engages in the cortical bone by having an increased thread height, a smaller lead-in angle on the bottommost portion, an outwardly tapered minor thread diameter so that all the threads end at least approximately 0.015" below the uppermost portion of the fixture, and a 0.010" highly polished collar above the threads that is approximately 0.010" larger in diameter than the major thread diameter. In a first embodiment, the implant fixture preferably has three equally spaced cutting flutes that run the length of the threaded portion and taper outwardly to match the taper angle of the minor diameter of the threads and stop below the 0.010" highly polished collar. With this configuration, the total threaded portion of the implant fixture mechanically grabs both cortical and cancellous bone giving it maximum mechanical stability without risking any bacterial leakage into the upper region of the bone. As the implant fixture is screwed into the bone, it compresses and cuts bone at three points separated by 120° as a result of engagement of the three cutting flutes and the outwardly tapered minor diameter of the thread.

In an alternative second embodiment, similar results are provided by a first cutting flute on the tapered entry portion of the threaded implant fixture and a second cutting flute on the portion of the screw containing the major diameter threads. This secondary cutting flute extends at least partially into the region of the fixture where the minor diameter of the threads is increasing.

Various other features, advantages and characteristics of the present invention will become apparent after a reading of the following detailed description thereof.

BRIEF DESCRIPTION OF THE DRAWINGS

The Figures depict the preferred embodiments of the present invention with like parts bearing like reference numerals, in which

FIG. 4 is a side view of the stepped drill bit used in the installation process of the present invention;

FIG. 4a is a perspective view of an end portion of the drill bit shown in FIG. 4;

FIG. 5a is a cross-sectional end view of a mandible drilled using the stepped drill bit of the present invention and awaiting installation of the fixture;

FIG. 5b is a cross-sectional end view of the mandible shown in FIG. 5a with the implant installed;

FIG. 8a is a side view of a third embodiment of the implant fixture of the present invention;

FIG. 8b is a schematic side view of that third embodiment with a drive element attached; and FIG. 8c is a top view of the drive element shown in FIG. 8b.

DETAILED DESCRIPTION OF THE PREFERRED EMBODIMENTS

Figure 3:
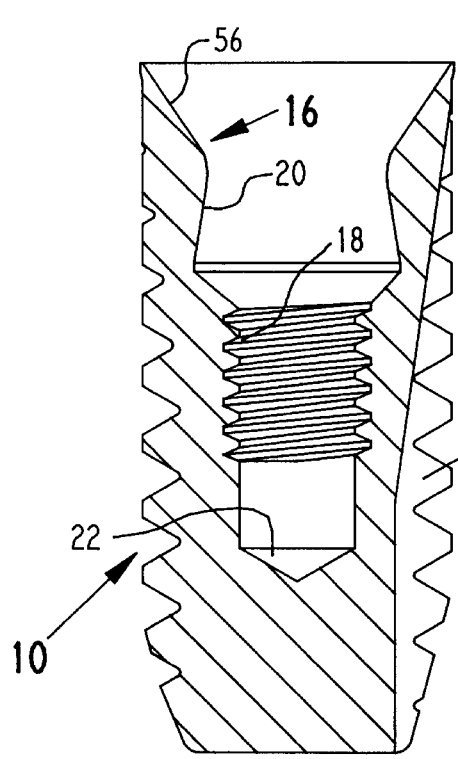
FIG. 3 is a cross-sectional side view as seen along line 3—3 of FIG. 2.
Figure 1:
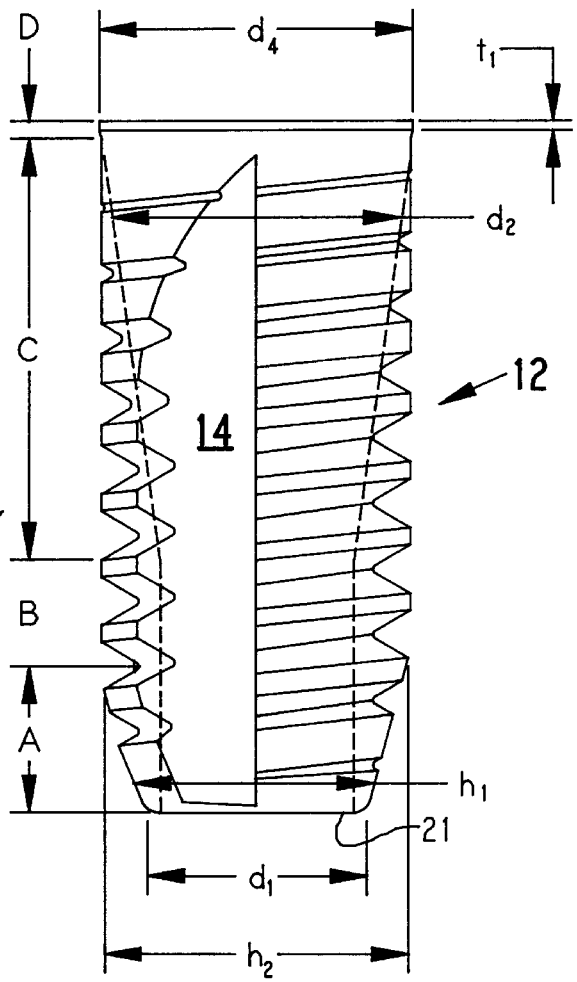
FIG. 1 is a side view of a first embodiment of the self-tapping dental implant of the present invention.
Figure 2:
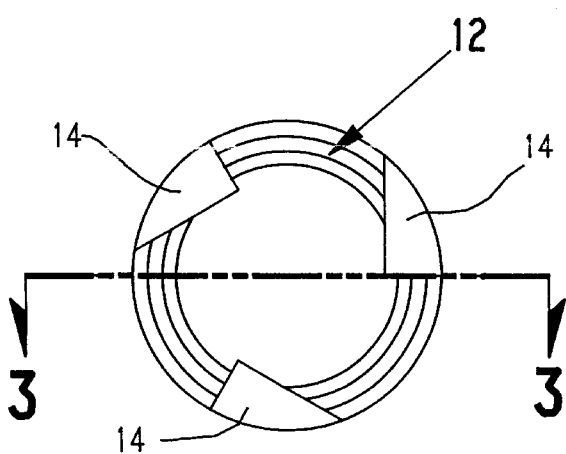
FIG. 2 is a bottom view of the embodiment shown in FIG. 1.

A first preferred embodiment of the self-tapping dental implant fixture of the present invention is depicted in FIGS. 1–3 generally at 10. A thread 12 is formed on the external periphery of fixture 10 for advancing and anchoring into an appropriate portion of a patient's jaw bone (this term shall be used herein to collectively refer to both mandibular and maxillary bone needing dental prosthetic implants). There are four zones A–D of fixture 10: zone A is the entry region having blunt end 21, a uniform minor or base diameter $d_1$ and a tapering major thread diameter or height $h_1$; zone B which has a uniform base diameter $d_1$ and a uniform major thread diameter $h_2$; zone C which has a tapering base diameter $d_2$ and a uniform thread height $h_2$; and, zone D which has a maximum diameter $d_4$ having an axial length or thickness $t_1$ on an uppermost region and is threadless throughout its thickness $t_1$.

Preferably three thread-cutting grooves 14 are cut diametrically (see FIG. 2) into threads 12 at 120° intervals about the periphery of fixture 10. In this embodiment, grooves 14 are continuous and each extends through at least portions of each and, preferably, through substantially all of zones A–C. Grooves 14 extend below the base diameter $d_1$ in zones A and B and taper in zone C at a rate which is most preferably substantially the same rate as outwardly tapering base diameter $d_2$. Grooves 14 do not extend into zone D so that maximum diameter $d_4$ of zone D can serve as a seal to prevent micro-migration into the bone around the implant 10. Because of the narrow profile of zone D, the threads of zone C can engage in the upper cortical bone as discussed below.

A longitudinal bore 16 formed in fixture 10 has a thread portion 18, an undercut 20, and a beveled counterbored region 22. Threaded portion 18 can be utilized to both attach the abutment (not shown) to fixture 10 and to attach a drive element 50 (FIG. 8b) utilizing a securement fastener 60 to permit drive rotation of the fixture 10 into the patient's jaw bone. A hex drive socket (not shown) engages external hex 52 to rotate fixture 10 into jaw bone 11 (FIG. 5b) with thread-cutting grooves 14 removing the bone tissue necessary to form female grooves for receiving threads 12. The method of installing implant 10 will be detailed in connection with FIGS. 4, 4a, 5a and 5b.

FIGS. 4 and 4a depict a stepped drill bit 30 useful in the installation process. Drill bit 30 has a tip 32 having a large included angle β. β is preferably in the range of between 110° and 125° and most preferably is an angle of 118°. This large included angle minimizes the amount of cortical bone 13 (FIGS. 5a and 5b) on the inferior border 15 that must be removed to accommodate the tapered entry region A of thread 12. The cortical bone 13 surrounding the spongier cancellous bone 17 in the center, is harder and the key to the present installation process is to maximize surface contact between the fixture 10 and cortical bone 13 to ensure optimum locking to reduce the possibility of loosening or thread backout. Chip removal slot 34 extends over a substantial portion of the drill bit's length to promote removal of debris. Tip 32 has a smaller diameter $d_5$ than the diameter $d_6$ of the main body 36 of drill bit 30. This also reduces the amount of cortical bone 13 removed from the inferior border 15. Leading edge 38 of drill tip 32 is hooked to increase its bite and to encourage chips to curl and breakoff. While FIGS. 4a and 4b depict the drill bit as having a single flute, bit 30 may have two or even three equally spaced flutes about its periphery.

As seen in FIG. 5a, stepped drill bit 30 is used to form a stepped hole 19 in jaw bone 11. The deepest portion 23 of hole 19 leaves adequate thickness of cortical bone 13 underlying (or overlying, in the case of maxilla) the implant fixture 10 to avoid breakthrough under maximum jaw pressure. Then a hex tool (not shown) is fitted upon external hex 52 (FIGS. 8b and 8c) and the self-tapping implant fixture 10 is rotated into the pre-drilled hole. By using a stepped drill, a second counterboring procedure is made unnecessary. Further, unlike some implant systems, the implant fixture 10 of the present invention taps its own threads in jaw bone 11 as it is rotated. This makes unnecessary an additional step of tapping a thread into the jaw bone prior to implant fixture insertion.

As seen in FIG. 5b, the tapered leading thread having diameter $d_1$ anchors in cortical bone 13 in inferior (or superior, in the case of maxilla) border 15. The highly polished threadless region of zone D which has a height of 0.010", engages superior cortical bone 15'. Implant 10 effectively maximizes the peripheral surface area in engagement with the higher density cortical bone and significantly reduces the possibility of loosening. Further, the maximum dimension $d_4$ at the upper reaches of the implant fixture 10 is threadless and exceeds the diameter $d_5$ by at least 0.010" reducing the risk of micromigration into the surgical region.

As the implant fixture 10 is permitted 4–6 months for the bone to grow around and capture it, the outward pressure exerted over substantially the entire length of the implant fixture 10 is believed to accelerate restorative bone growth.

Figure 6:
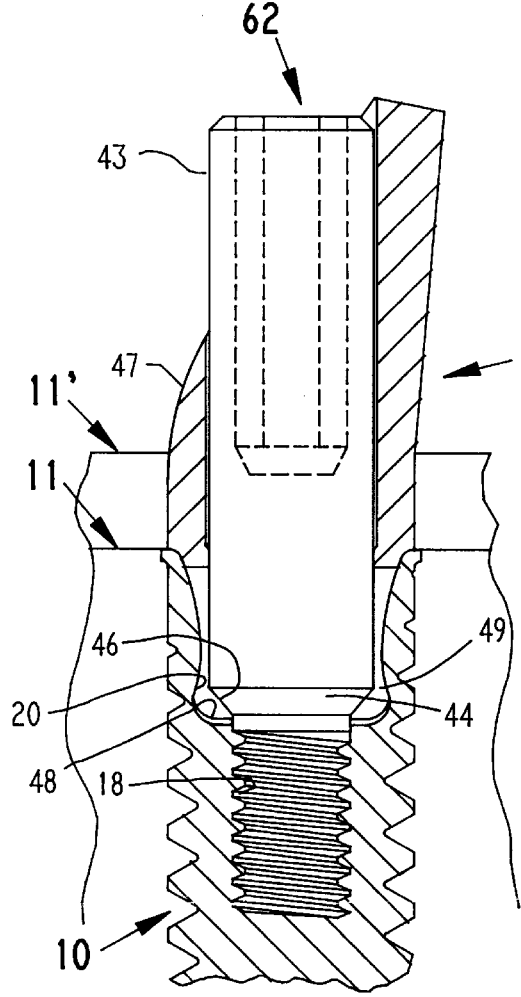
FIG. 6 is a break away cross-sectional side view showing an implant with fixture attached.

FIG. 6 depicts implant 10 having an abutment 40 being initially installed in jaw bone 11 and secured thereto by securement fastener 62. The position of skin cover over bone 11 is shown at 11'. Tapered surface 44 on member 62 engages tapered surfaces 46 on abutment 40 forcing rear surfaces 48 of fingers 49 (as taught in U.S. Pat. No. 5,302,125) underneath undercut 20 creating mechanical interlock between fixture 10 and abutment 40 making it impossible for these elements to be separated without removal of threaded member 62. Following tightening of threaded member 62, the upper protruding portion 43 may be ground off to match the slope of surface 47 on abutment 40. A dental prosthesis (not shown) is then attached to abutment 40, as by casting it in place from a moldable material.

Figure 7B:
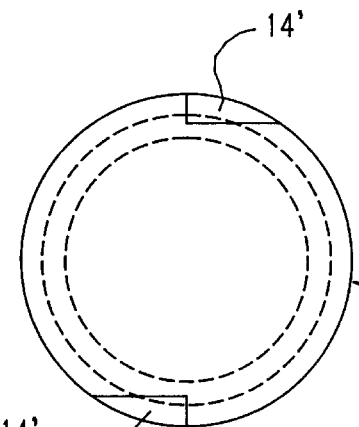
FIG. 7b is a top view of the second embodiment of the fixture.
Figure 7A:
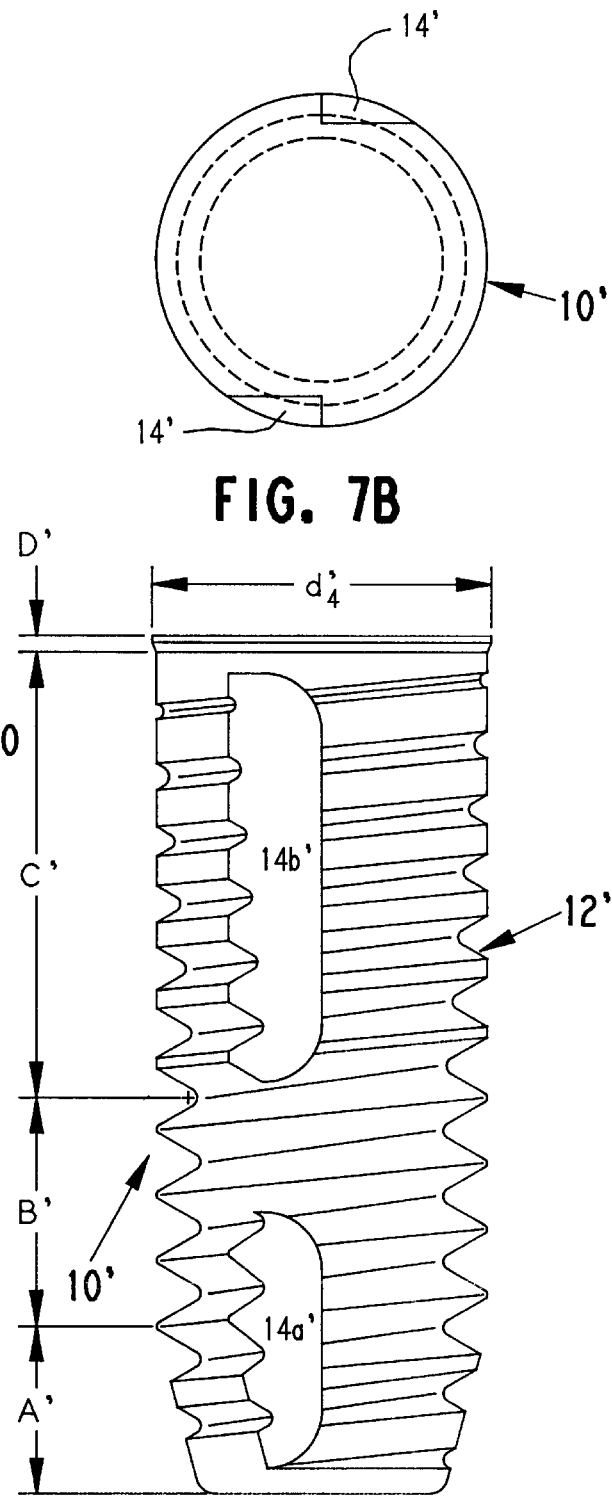
FIG. 7a is a side view of a second embodiment of the fixture of the present invention.

FIGS. 7a and 7b depict a second embodiment 10' of the present invention. In this embodiment, thread-cutting grooves 14' are formed in two portions. First portion 14a' begins in zone A which has uniform minor diameter $d_1$ and tapering major thread diameter $h_1$ and extends into zone B which has the uniform minor thread diameter $d_1$ and uniform major thread height $h_2$. Second thread-cutting groove portion 14b' extends substantially the entire length of zone C. This second thread-cutting groove 14b' tapers outwardly substantially at the same rate as minor thread diameter of zone C. These tapers serve to expand the diameter of the tapped hole in the proximal corticular bone 15' as well as the cancellous bone 17 while the tapered zone A is tapping and anchoring in distal corticular bone 15. Because diameter $d_4$ of highly polished segment of zone D is the maximum diameter of implant 10', this region can serve to seal the bone region around the implant 10' against micro-migration. Further, it is believed the larger compressive pressure exerted by threads 12' induces more rapid bone growth following installation of the implant 10'. As shown in FIG. 7b, grooves 14' may be limited to two diametrically opposed thread-cutting grooves, although the three equally spaced grooves of the first embodiment is actually preferred.

FIGS. 8a, 8b, and 8c depict a third embodiment of the invention. The embodiments of FIGS. 1–7b depict systems in which flexible fingers 49 are formed on abutment 40. However, it may be desirable in certain applications to form the flexible fingers 49" directly on the top portion of implant 10", thereby reversing the undercut/locking roles performed by the interengaged portions of implant 10" and abutment (not shown). While this embodiment is shown with the split groove configuration (14a" and 14b") of the second embodiment, it will be understood a single continuous groove of the type utilized in the FIG. 1 embodiment could be used, as well. As has previously been discussed, FIGS. 8b and 8c show attachment of an external hex drive element 50 by securement fastener 60. This provides an enlarged, and therefore, superior drive surface in the form of hex surfaces 52 so the drive force can be more widely distributed than if an internal hex is used. Further, by providing the driver 50 on a separate element, the surfaces can be more robust since element 50 can be made of a higher strength material and need not be of a biomechanical material since it shall be removed once implant 10" has been installed.

Various changes, alternatives, and modifications to the specific embodiments discussed above will become apparent to one of ordinary skill in the art following a reading of the foregoing specification. It is intended that all such changes, alternatives, and modifications as come within the scope of the appended claims be considered part of the present invention.

We claim:

1. A self-tapping implantable dental fixture used to secure a dental prosthesis in a patient's jaw comprising
   a) a generally cylindrical member;
   b) a substantially blunt end on said cylindrical member;
   c) a threaded region on an external periphery of said cylindrical member extending throughout a substantial portion of said member's length, a major portion of said threaded region having a thread with a uniform major diameter, said threaded region having a segment with a tapering minor diameter over a major portion of its length such that said thread has a varying height throughout said segment;
   d) a plurality of thread-cutting slots cut substantially radially into said threads substantially throughout a significant portion of the length of said threaded region for tapping a receiving thread in a patient's jaw bone;
   e) a highly polished collar portion formed above said threaded region adjacent thereto, said collar portion having a diameter which slightly exceeds said uniform major diameter of said threaded region;

whereby said thread-cutting slots which are formed on a trailing portion of said threaded region enlarge a hole in an upper cortical bone and said highly polished collar portion serves to seal an uppermost opening in said jaw bone against micro-migration.

2. The dental fixture of claim 1 wherein said minor diameter tapers substantially uniformly throughout said portion of said threaded region which has a tapering minor diameter.

3. The dental fixture of claim 1 wherein said plurality of said thread-cutting slots comprise three slots equally spaced about the periphery of said generally cylindrical member.

4. The dental fixture of claim 1 wherein each of said plurality of thread-cutting slots tapers outwardly over the portion of said threaded portion having a tapering minor diameter at substantially the same angle of taper as said minor diameter.

5. The dental fixture of claim 1 further comprising a tapered entry segment extending from said blunt end, said entry segment having threads with a substantially constant minor diameter and a substantially uniformly tapering major diameter.

6. The dental fixture of claim 5 wherein each of said thread-cutting slots comprises a first slot portion extending over a major portion of said entry segment and a second coaxial slot portion extending over a major portion of said segment with a tapering minor diameter.

7. The dental fixture of claim 6 wherein said second slot portion tapers outwardly at substantially the same angle as said minor diameter.

8. A process for installing a dental prosthetic implant in a jaw bone comprising the steps of
   a) drilling a stepped hole into said jaw bone, said stepped hole having a leading portion having a first diameter and a trailing portion with a second greater diameter, said first leading portion extending through a cancellous bone portion into a first distal corticular bone portion and the second trailing portion extending out of said cancellous bone portion into a second proximate corticular bone portion;
   b) installing a threaded, self-tapping implant such that a leading segment anchors in said distal corticular bone and a trailing segment anchors in said proximate corticular bone, whereby said trailing segment includes an unthreaded portion of maximum diameter on said implant which serves to seal the region around said implant against micro-migration into said jaw bone.

* * * * *